(12) United States Patent
Zablocki et al.

(10) Patent No.: US 6,180,615 B1
(45) Date of Patent: Jan. 30, 2001

(54) PROPARGYL PHENYL ETHER $A_{2A}$ RECEPTOR AGONISTS

(75) Inventors: Jeff A. Zablocki; Venkata P. Palle, both of Mountain View; Elfatih O. Elzein, Freemont; Grigory Nudelman, Pacifica, all of CA (US)

(73) Assignee: CV Therapeutics, Inc., Palo Alto, CA (US)

( * ) Notice: Under 35 U.S.C. 154(b), the term of this patent shall be extended for 0 days.

(21) Appl. No.: 09/338,183

(22) Filed: Jun. 22, 1999

(51) Int. Cl.[7] .................. A61K 31/70; C07H 19/167
(52) U.S. Cl. .................. 514/46; 536/27.22; 536/27.63
(58) Field of Search .................. 536/27.22, 27.63; 514/116

(56) References Cited

U.S. PATENT DOCUMENTS

| | | | |
|---|---|---|---|
| 4,956,345 | * | 9/1990 | Miyasaka et al. .................. 514/46 |
| 5,189,027 | * | 2/1993 | Miyashita et al. .................. 514/46 |
| 5,270,304 | * | 12/1993 | Kogi et al. .................. 514/46 |
| 5,459,254 | * | 10/1995 | Yamaguchi et al. .................. 536/27.11 |
| 5,593,975 | | 1/1997 | Cristalli . |
| 5,705,491 | * | 1/1998 | Yamada et al. .................. 514/46 |
| 5,770,716 | * | 6/1998 | Khan et al. .................. 536/23.1 |
| 5,939,543 | * | 8/1999 | Morozumi et al. .................. 536/27.63 |

FOREIGN PATENT DOCUMENTS 965411    4/1975  (CA) .

OTHER PUBLICATIONS

Cristalli et al., "2–Alkynyl Derivatives of Adenosine–5'–N–Ethyluronamide: Selective $A_2$ Adenosine Receptor Agonists with Potential Inhibitory Activity on Platelet Aggregation," *Journal of Medicinal Chemistry*, 37(11), 1720–1726 (May 27, 1994).*

Matsuda et al., "Nucleosides and Nucleotides. 103. 2–Alkynyladenosines: A Novel Class of Selective Adenosine $A_2$ Receptor Agoinsts with Potential Antihypertensive Effects," *Journal of Medicinal Chemistry*, 35(2), 241–252 (Jan. 24, 1992).*

Marumoto, et al., "Synthesis and Enzymatic Activity of Adenosine 3',5'–Cyclic Phosphate Analogs", *Chem.. Pharm. Bull.* 27(4) 990–1003 (1979).

Persson, et al., "Synthesis and Antiviral Effects of 2–Heteroaryl Substituted Adenosine and 8–Heteroaryl Substituted Guanosine Derivatives", *Bioorganic & Medicinal Chemistry*, 3:1377–1382 (1995). (Issue No. 10).

Mager, et al., "Molecular simulation applied to 2–(N'alkylidenehydrazino)–and 2–(N'–aralkylidenehydrazino) adenosine $A_2$ Agnonists", *Eur J. Med. Chem*, 30:15–25 (1995).

* cited by examiner

Primary Examiner—Gary Geist
Assistant Examiner—L. E. Crane
(74) Attorney, Agent, or Firm—McDonnell Boehnen Hulbert & Berghoff

(57) ABSTRACT

2-adenosine propargyl phenyl ether compositions having the following formula:

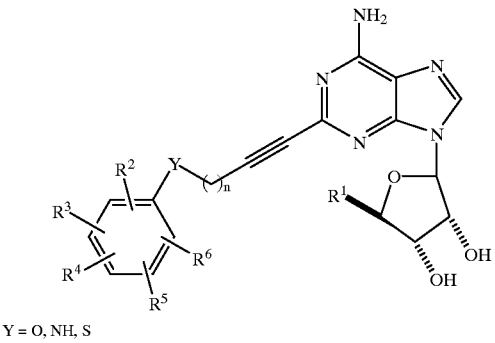

Y = O, NH, S and methods for using the compositions as $A_{2A}$ receptor agonists to stimulate mammalian coronary vasodilatation for therapeutic purposes and for purposes of imaging the heart.

25 Claims, No Drawings

PROPARGYL PHENYL ETHER A$_{2A}$ RECEPTOR AGONISTS

BACKGROUND OF THE INVENTION

1. Field of Invention

This invention includes 2-adenosine propargyl phenyl ether compositions that are useful as A$_{2A}$ receptor agonists. The compositions of this invention are vasodialating agents that are useful as heart imaging agents that aid in the identification of mammals, and especially humans who are suffering from disorders such poor coronary perfusion which is indicative of coronary artery disease (CAD). The compositions of this invention can also be used as therapeutics for coronary artery disease.

2. Description of the Art

Pharmacological stress is frequently induced with adenosine or dipyridamole in patients with suspected CAD before imaging with Tl scintigraphy or echocardiography. Both drugs effect dilation of the coronary resistance vessels by activation of cell surface A$_2$ receptors. Although pharmacological stress was originally introduced as a mean of provoking coronary dilation in patients unable to exercise, several studies have shown that the prognostic value of $^{201}$Tl or echocardiographic imaging in patients subjected to pharmacological stress with adenosine of dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine A$_{2B}$ and A$_3$ receptors are involved in a mast cell degranulation and, therefore, asthmatics are not give the non-specific adenosine agonists to induce a pharmacological stress test. Additionally, adenosine stimulation of the A$_1$ receptor in the atrium and A-V mode will diminish the S-H interval which can induce AV block. (N. C. Gupto et al.; *J. Am Coll. Cardiol;* (1992) 19: 248–257). Also, stimulation of the adenosine A1 receptor by adenosine may be responsible for the nausea since the A$_1$ receptor is found in the intestinal tract. (J. Nicholls et al.; *Eur. J. Pharm.*(1997) 338(2) 143–150).

Animal data suggests that specific adenosine A$_{2A}$ subtype receptors on coronary resistance vessels mediate the coronary dilatory responses to adenosine, whereas subtype A$_{2B}$ receptor stimulation relaxes peripheral vessels (note: the latter lowers systemic blood pressure). As a result there is a need for pharmaceutical compositions that are A$_{2A}$ receptor agonists that have no pharmacological effect as a result of stimulating the A$_1$ receptor in vivo. Furthermore, there is a need for A$_{2A}$ receptor agonists that have a short half-life, and that are well tolerated by patients undergoing pharmacological coronary stress evaluations.

SUMMARY OF THE INVENTION

In one aspect, this invention includes 2-adenosine propargyl phenyl ether compositions that are useful A$_{2A}$ receptor agonists.

In another aspect, this invention includes pharmaceutical compositions including 2-adenosine propargyl phenyl ether compounds that are well tolerated with few side effects.

Still another aspect of this invention are 2-adenosine propargyl phenyl ether compositions that can be easily used in conjunction with radioactive imaging agents to facilitate coronary imaging.

In one embodiment, this invention includes 2-adenosine propargyl phenyl ether compositions having the following formula:

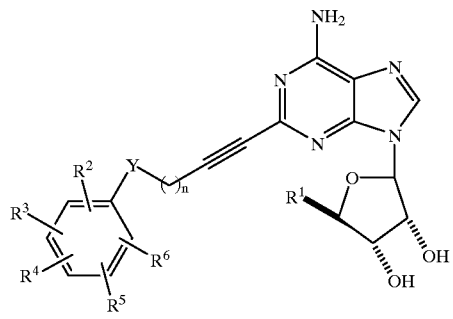

Y = O, NH, S

In another embodiment, this invention includes methods for using compositions of this invention to stimulate coronary vasodilatation in mammals, and especially in humans, for stressing the heart induced steal situation for purposes of imaging the heart.

In still another embodiment, this invention is pharmaceutical compositions of matter comprising one or more compositions of this invention and one or more pharmaceutical excipients.

DESCRIPTION OF THE CURRENT EMBODIMENT

The compositions of this invention include a class of propargyl phenyl ether substituted 2-adenosine compounds having the following formula:

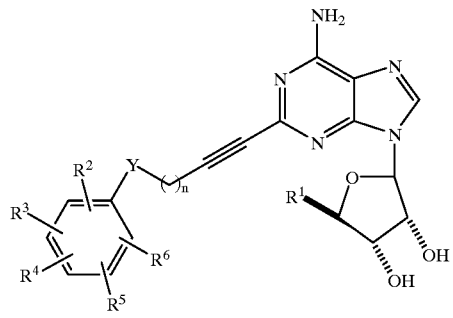

Y = O, NH, S wherein n 1 or 2;

Y=O, N and S;

R$^1$ is —CH$_2$OH and —C(=O)NR$^7$R$^8$;

R$^2$, R$^3$, R$^4$, R$^5$, and R$^6$ are each individually selected from the group consisting of hydrogen, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON (R$^{20}$)$_2$, N(R$^{20}$)$_2$NR$^{20}$COR$^{22}$, NR$^{20}$CO$_2$R$^{22}$, NR$^{20}$CON (R$^{20}$)$_2$, NR$^{20}$C(NR$^{20}$)NHR$^{23}$, COR$^{20}$, CO$_2$R$^{20}$, CON (R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, OCON(R$^{20}$)$_2$, C$_{1-15}$ alkyl, C$_{2-15}$ alkenyl, C$_{2-15}$ alkynyl, heterocyclyl, aryl, and heteroaryl, which alkyl, alkenyl, alkynyl, C$_{1-15}$ alkoxy, aryl, heterocyclyl, and heteroaryl are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substitution substituent is further optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^7$ and R8 are each independently selected from H, and $C_{1-15}$ alkyl optionally substituted with from 1 to 2 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R_{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(^{20})_2$ and each optional heteroaryl, aryl, and heterocyclyl substituent is further optionally substituted with halo, $NO_2$, alkyl, $CF_3$, amino, monoalkylamino or dialkylamino, alkylamide, arylamide or heteroarylamide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is selected from the group consisting of $C_{1-15}$ alkyl, $C_{2-15}$ alkenyl, $C_{2-15}$ alkynyl, heterocyclyl, aryl, and heteroaryl which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, —O—$C_{1-6}$ alkyl, $CF_3$, and heteroaryl.

Preferably, $R^1$ is $CH_2OH$ or $C(O)NHEt$; $R^2$, $R^3$, $R^4$, $R^5$, and $R^6$ are each individually selected from the group consisting of hydrogen, halo, $CF_3$, CN, $OR^{20}$, $C_{1-4}$ alkyl, heterocyclyl, and aryl which alkyl and aryl are each optionally substituted with aryl; and $R^{20}$ is a member selected from the group consisting of H and $C_{1-3}$ alkyl.

More preferably one subsitutent selected from $R^2$, $R^3$, $R^4$, $R^5$, and $R^6$ the heterocyclyl that is fused five to seven membered ring containing 1 to 3 heteroatoms selected from O, N, and S, even more preferably, the 1 to 3 heteroatoms are two oxygen atoms, and most preferably, two oxygen atoms with points of attachment at the 2 and 3 position.

In a further preferred embodiment, at least one, more preferably two, and even more preferably 3 to 4 of the substituents selected from the group consisting of $R^2$, $R^3$, $R^4$, $R^5$, and $R^6$ are hydrogen.

In still a further preferred embodiment, the compounds of this invention are selected from (4S,2R,3R,5R)-2-{6-amino-2-[3-(2-phenylphenoxy)prop-1-ynyl]purin-9-yl}-5-(hydroxymethyl)oxolane-3,4-diol, (4S,2R,3R,5R)-2-[6-amino-2-(3-phenoxyprop-1-ynyl)purin-9-yl]-5-(hydroxymethyl)oxolane-3,4-diol, 4-(3-{9-[(4S,2R,3R,5R)-3,4-dihydroxy-5-(hydroxymethyl)oxolan-2-yl]-6-aminopurin-2-yl}prop-2-ynyloxy)benzenecarbonitrile, (4S, 2R,3R,5R)-2-{6-amino-2-[3-(4-phenylphenoxy)prop-1-ynyl]purin-9-yl}-5-(hydroxymethyl)oxolane-3,4-diol, (4S, 2R,3R,5R)-2-(6-amino-2-{3-[2-benzylphenoxy]prop-1-ynyl}purin-9-yl)-5-(hydroxymethyl)oxolane-3,4-diol, 2-[2-(3-(2H-benzo[2,3-d]1,3-dioxolen-4-yloxy)prop-1-ynyl)-6-aminopurin-9-yl](4S,2R,3R,5R)-5-(hydroxymethyl) oxolane-3,4-diol, (4S,2R,3R,5R)-2-(6-amino-2-{3-[3,5-bis(tert-butyl)phenoxy]prop-1-ynyl}purin-9-yl)-5-(hydroxymethyl)oxolane-3,4-diol, and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methylcyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than ones carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'" R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein of acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in Schemes 1–3 below. Compounds having the general formula IV (Scheme 1) can be prepared by the palladium mediated cross-coupling of compound 1 with alkynyl derivatives (Y=O, NH, S) represented by the formula III (Scheme 1) in the presence or absence of copper salts (Matsuda et al, Chem. Phar. Bull, (1985), 33, 19766–19769; Kochetkov et al., Organic Chemistry of Nucleic Acids, Part B, Plenum Press, New York, (1972), 333; Nair, et al., Tet. Lett. (1990), 31, 807–810). In some cases compound III can be obtained from commercial sources. Examples of commercially available Compound III compounds include phenyl propargyl ether, 3-(2,6-dischlorophenoxy)prop-1-yne, 3-(4-cyanophenoxy)prop-1-yne, 3-(4-carboxyethylphenoxy)prop-1-yne, 3-(4-cyanophenoxy)-3-methyl-but-1-yne, and phenyl propargyl sulfide. Compound III can be prepared either by the reaction of propargyl or homo-propargyl bromide with substituted phenols, thiophenols and anilines using a base (e.g. potassium carbonate) in an appropriate solvent (e.g. DMF, acetone). Specifically, when Y=NH, the aniline starting

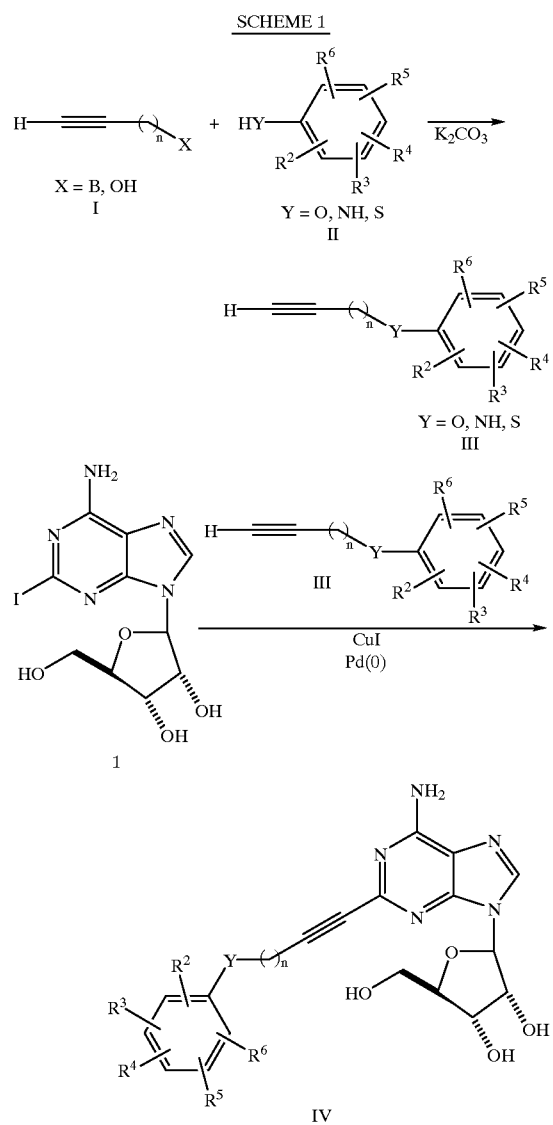

material can be activated by making a trifluoroacetamide followed by alkylation. An alternative synthesis of compound III can be accomplished by reacting propargyl or homopropargyl alcohols with phenols and thiophenols under Mitsunobu reaction conditions (O. Mitsunobu, Bull. Chem. Soc. Jpn., (1967), 40, 2380; A. Hassner, J. Org. Chem. (1990), 55, 2243).

Compounds with general formula VII can be prepared as shown in Scheme 2. Compound 2, which can be obtained by reacting compound 1 with 2,2-dimethoxypropane in the presence of an acid, can be oxidized to the carboxylic acid 3, based on structurally similar compounds, using potassium permanganate or pyridinium chlorochromate, or TEMPO etc., (M. Hudlicky, (1990) Oxidations in Organic Chemistry, ACS Monographs, American Chemical Society, Washington, D.C.; B. Cox et al, WO 9828319) to compound 3. Reaction of a primary or secondary amine with the formula HNR$^6$R$^7$, and compound 3 using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound V. Compound VI can be prepared by the palladium mediated cross-coupling of compound V with alkynyl derivatives (Y=O, N, S) represented by the formula III (Scheme 1), in an appropriate solvent (e.g. DMF, acetone) in the presence or absence of copper salts. Deprotection of compound VI can be performed by heating with 80% aqueous acetic acid (T. W. Greene and P. G. M. Wuts, (1991) Protective Groups in Organic Synthesis, A. Wiley-Interscience publication) or with anhydrous hydrochloric acid (4N) to obtain compound VII.

SCHEME 2

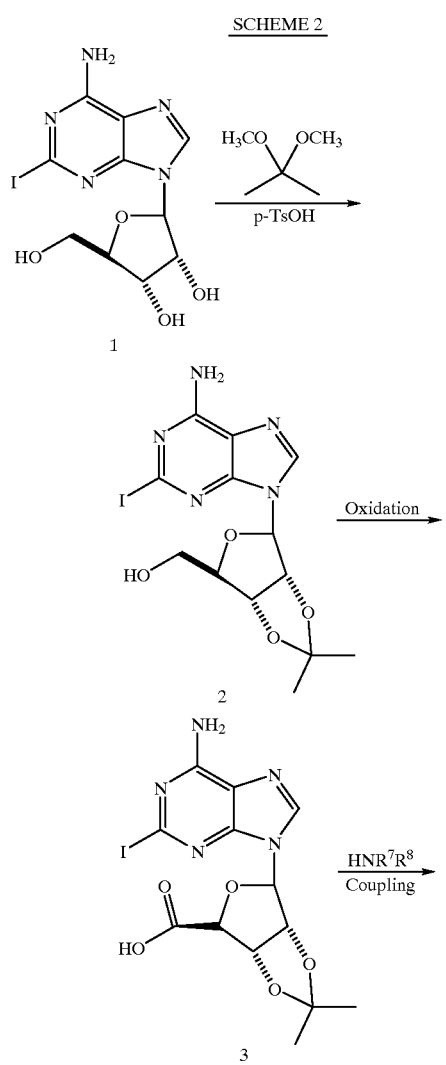

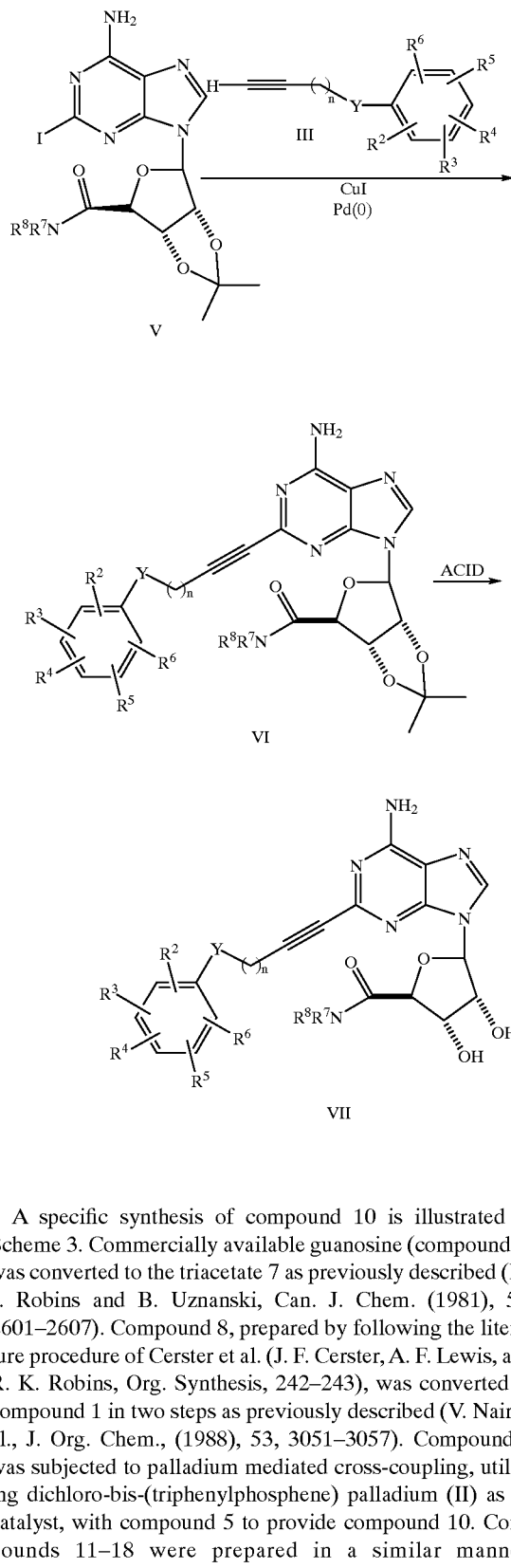

A specific synthesis of compound 10 is illustrated in Scheme 3. Commercially available guanosine (compound 6) was converted to the triacetate 7 as previously described (M. J. Robins and B. Uznanski, Can. J. Chem. (1981), 59, 2601–2607). Compound 8, prepared by following the literature procedure of Cerster et al. (J. F. Cerster, A. F. Lewis, and R. K. Robins, Org. Synthesis, 242–243), was converted to compound 1 in two steps as previously described (V. Nair et al., J. Org. Chem., (1988), 53, 3051–3057). Compound 1 was subjected to palladium mediated cross-coupling, utilizing dichloro-bis-(triphenylphosphene) palladium (II) as ax catalyst, with compound 5 to provide compound 10. Compounds 11–18 were prepared in a similar manner.

SCHEME 3

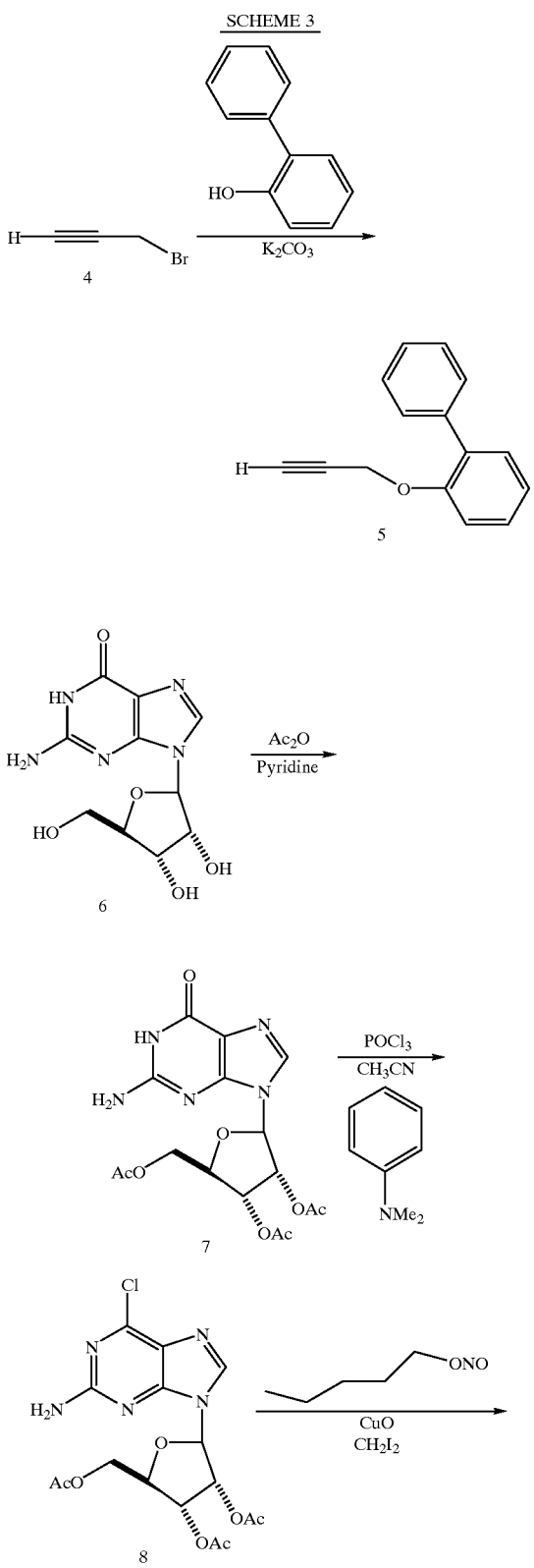

The methods used to prepare the compounds of this invention are not limited to those described above. Additional methods can be found in the following sources and are included by reference (J. March, Advanced Organic Chemistry; Reaction Mechanisms and Studies (1992), A Wiley Interscience Publications and J. Tsuji, Palladium Reagents and Catalyst, Innovations in Organic Synthesis (1996), John Wiley & Sons Publications).

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine $A_1$ receptors in the atrium and AV-node and/or $A_{2B}$ receptors in peripheral vessels, thus avoiding undesirable side-effects. Upon administration in a therapeutic amount, the compositions of this invention cause coronary blood vessels to vasodilate to induce coronary steal wherein healthy coronary vessels steal blood from unhealthy vessels resulting in lack of blood flow to heart tissues. Coronary imaging then identified coronary regions with healthy and unhealthy blood flow. Lower doses of the $A_{2A}$ agonists may provide beneficial coronary vasodilatation (less severe) in the treatment of chronic CAD.

As $A_{2A}$ agonists, the compositions of this invention are also useful in adjunctive therapy with angioplasty to induce dilation, inhibit platelet aggregation, and as a general anti-inflammatory agent. $A_{2A}$ agonists, such as the compositions of this invention, can provide the therapeutic benefits described above by preventing neutrophil activation (Purinergic Approaches in Experimental Therapeutics K. A. Jacobson and M. F. Jarvis 1997 Wiley, New York). The compounds of this invention are also effective against a condition called no-reflow in which platelets and neutrophils aggregate and block a vessel. As $A_{2A}$ agonists, the compositions of this invention are effective against no-reflow by preventing neutrophil and platelet activation (e.g., they are believed to prevent release of superoxide from neutrophils). As $A_{2A}$ agonists, the compositions of this invention are also useful as cardioprotective agents through their anti-inflammatory action on neutrophils. Thus, in situations when the heart will go through an ischemic state such as a transplant, they will be useful.

This invention also includes pro-drugs of the above-identified $A_{2A}$ agonists. A pro-drug is a drug that has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non-specific proteinase; or (3) derivatives that accumulate at a site of action through membrane selection or a pro-drug form or modified pro-drug form, or any combination of (1) to (3) above.

The compositions may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in therapeutic amounts.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

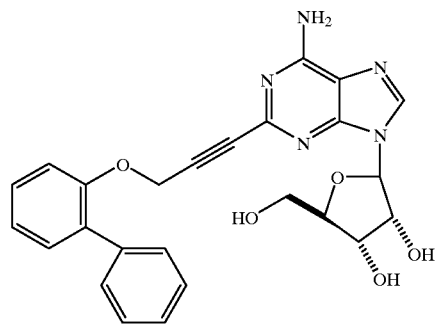

(4S,2R,3R,5R)-2-{6-amino-2-[3-(2-phenylphenoxy)prop-1-ynyl]purin-9-yl}-5-(hydroxymethyl)oxolane-3,4-diol (10)

Synthesis of 2-phenyl-1-prop-2-ynyloxybenzene (compound 5)

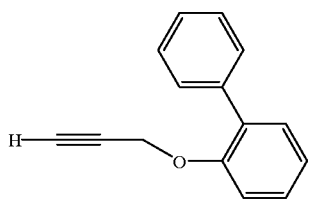

To a solution of propargyl bromide (80% solution in toluene, 500 δ 3.36 mmol) in acetone (15 ml) at 23° C. was added 2-phenyl phenol (316 mg, 1.86 mmol) and potassium carbonate (1.05 g, 7.61 mmol). After being stirred in a sealed reaction vial at 65° C. for 14 hours, the reaction was concentrated in vacuo, the residue purified by flash chromatography (ethyl acetate:hexane: 9:1) to afford compound 5 in 95% yield. $^1$H NMR(CDCl$_3$) δ 2.45–2.55 (m, 1H), 4.60–4.70 (m, 2H), 6.99–7.43 (m, 9H).

Synthesis of (4S,2R,3R,5R)-2-[6-amino-2-(3-phenoxyprop-1-ynyl)purin-9-yl]-5-(hydroxymethyl)oxolane-3,4-diol (compound 10)

To a solution of (4S,2R,3R,5R)-2-(6-amino-2-iodopurin-9-yl)-5-(hydroxymethyl)oxolane-3,4-diol (compound 1) (50 mg, 0.126 mmol) and prop-2-ynyloxybenzene (22 δ, 0.1605 mmol) in N,N-dimethylformamide (1 ml) and triethylamine (21 δ, 16.065 mmol) at 23° C. was added copper iodide (5 mg, 0.026 mmol) and dichlorobis(triphenylphosphine)palladium(II) (22 mg, 0.031 mmol) catalyst. After being stirred in a sealed reacti-vial at 80 C for 6 hours, the reaction was concentrated in vacuo, the residue purified by preparatory thin layer chromatography (methylene chloride:methanol 9:1) to afford compound 10 (9.6 mg, 0.024 mmol) in 20% yield. $^1$H NMR(CDCl$_3$:CD$_3$OD 9:1) δ 3.02–3.04 (m, 1H), 3.07 (s, 1H), 3.55, 3.74 (dd, 2H), 4.02 (s, 1H), 4.11–4.13 (m, 1H), 4.48–4.52 (m, 1H), 4.72 (s, 2H), 5.65 (d, 1H), 6.75–6.82 (m, 3H), 7.08–7.12 (m, 2H), 7.94 (s, 1H).

EXAMPLE 2

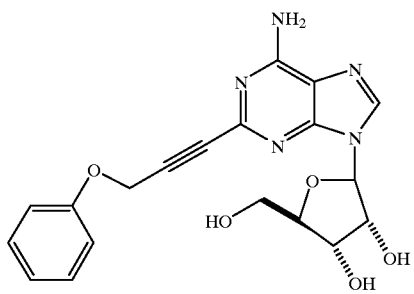

(4S,2R,3R,5R)-2-[6-amino-2-(3-phenoxyprop-1-ynyl)purin-9-yl]-5-(hydroxymethyl)oxolane-3,4-diol (11)

Compound 11 was prepared in the manner of compound 10. $^1$H NMR (CDCl$_3$:CD$_3$OD 9:1) δ3.02–3.04 (m, 1H), 3.07 (s, 1H), 3.55, 3.74 (dd, 2H), 4.02 (s, 1H), 4.11–4.13 (m, 1H), 4.48–4.52 (m, 1H), 4.72 (s, 2H), 5.65 (d, 1H), 6.75–6.82 (m, 3H), 7.08–7.12 (m, 2H), 7.94 (s, 1H). ), 4.48–4.52 (m, 1H), 4.72 (s, 2H), 5.65 (d, 1H), 6.90–7.00 (m, 1H), 7.10–7.15 (m, 1H), 7.15–7.32 (m, 5H), 7.35–7.45 (m, 2H), 7.94 (s, 1H).

EXAMPLE 3

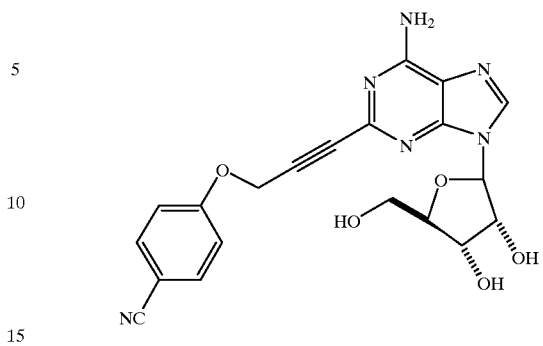

4-(3-{9-[(4S,2R,3R,5R)-3,4-dihydroxy-5-(hydroxymethyl)oxolan-2-yl]-6-aminopurin-2-yl}prop-2-ynyloxy)benzenecarbonitrile (12)

Compound 12 was prepared in the manner of compound 10. $^1$H NMR(CDCl$_3$:CD$_3$OD 9:1) δ3.55 (d, 1H), 3.70 (d, 1H), 4.05–4.07 (m, 1H), 4.10–4.12 (m, 1H), 4.48 (dd, 1H), 4.80 (s, 2H), 5.65 (d, 1H), 6.90 (d, 2H), 7.45 (d, 2H), 7.95 (s, 1H)

EXAMPLE 4

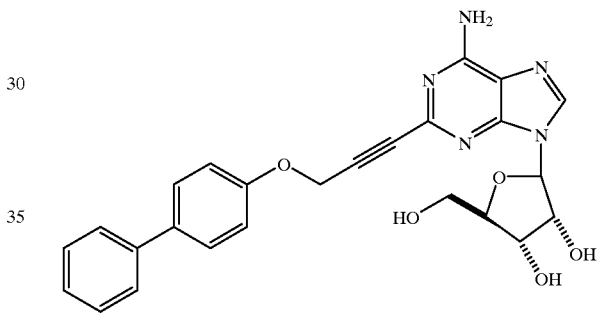

(4S,2R,3R,5R)-2-{6-amino-2-[3-(4-phenylphenoxy)prop-1-ynyl]purin-9-yl}-5-(hydroxymethyl)oxolane-3,4-diol (13)

Compound 13 was prepared in the manner of compound 10. $^1$H NMR(CDCl$_3$:CD$_3$OD 9:1) δ3.02–3.04 (m, 1H), 3.07 (s, 1H), 3.55, 3.74 (dd, 2H), 4.02 (s, 1H), 4.11–4.13 (m, 1H), 4.48–4.52 (m, 1H), 4.72 (s, 2H), 5.65 (d, 1H), 6.90–7.00 (m, 1H), 7.10–7.15 (m, 1H), 7.15–7.32 (m, 5H), 7.35–7.45 (m, 2H), 7.94 (s, 1H).

EXAMPLE 5

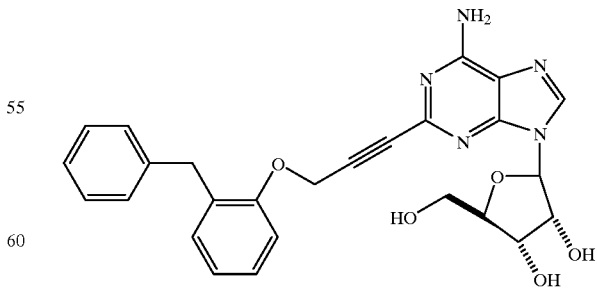

(4S,2R,3R,5R)-2-(6-amino-2-{3-[2-benzylphenoxy]prop-1-ynyl}purin-9-yl)-5-(hydroxymethyl)oxolane-3,4-diol (14)

Compound 14 was prepared in the manner of compound 10. $^1$H NMR(CDCl$_3$:CD$_3$OD 9:1) δ3.02–3.04 (m, 1H), 3.07

(s, 1H), 3.55, 3.74 (dd, 2H), 3.92 (s, 2H), 4.02 (s, 1H), 4.11–4.13 (m, 1H), 4.48–4.52 (m, 1H), 4.72 (s, 2H), 5.65 (d, 1H), 6.80–6.88 (m, 1H), 6.96–7.01 (m, 2H), 7.15–7.22 (m; 6H), 7.94 (s, 1H).

EXAMPLE 6

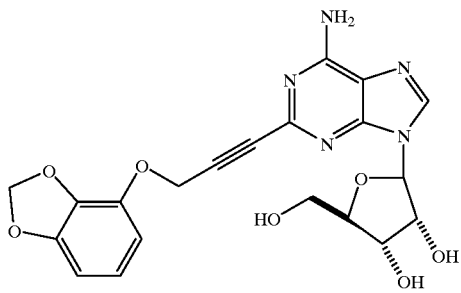

2-[2-(3-(2H-benzo[2,3-d]1,3-dioxolen-4-yloxy)prop-1-ynyl)-6-aminopurin-9-yl](4S,2R,3R,5R)-5-(hydroxymethyl)oxolane-3,4-diol (15)

Compound 15 was prepared in the manner of compound 10. $^1$H NMR(CDCl$_3$:CD$_3$OD 9:1) 3.61 (d, J=13.2 Hz, 1H), 3.78 (d, J=13.2 Hz, 1H) 4.10–4.12 (m, 1H), 4.21–4.22 (m, 1H), 4.58–4.59 (m, 1H), 4.68 (s, 2H, O—CH2—O), 5.73–5.75 (m, 3H), 6.30 (d, J=8.4 Hz, 2H), 6.45 (s, 1H), 6.54 (d, J=8.4 Hz, 2H), 8.07 (s, 1H).

EXAMPLE 7

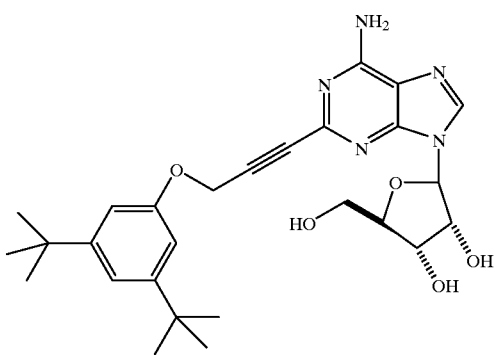

(4S,2R,3R,5R)-2-(6-amino-2-{3-[3,5-bis(tert-butyl)phenoxy]prop-1-ynyl}purin-9-yl)-5-(hydroxymethyl)oxolane-3,4-diol (16)

Compound 16 was prepared in the manner of compound 10. $^1$H NMR(CDCl$_3$:CD$_3$OD 9:1) δ1.22 (s, 9H), 3.02–3.04 (m, 1H), 3.07 (s, 1H), 3.55, 3.74 (dd, 2H), 4.02 (s, 1H), 4.11–4.13 (m, 1H), 4.48–4.52 (m, 1H), 4.72 (s, 2H), 5.65 (d, 1H), 6.78 (s, 2H), 6.99 (s, 1H), 7.94 (s, 1H).

EXAMPLE 8

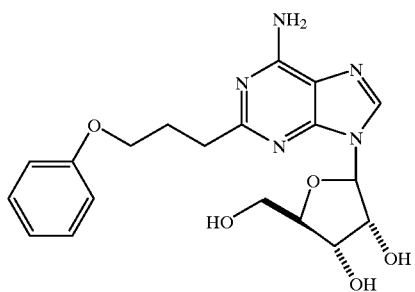

(4S,2R,3R,5R)-2-[6-amino-2-(3-phenoxypropyl)purin-9-yl]-5-(hydroxymethyl)oxolane-3,4-diol (17)

Compound 17 was prepared in the manner of compound 10. $^1$H NMR(CDCl$_3$:CD$_3$OD 9:1) δ2.15–2.25 (m, 2H), 3.02–3.04 (m, 1H), 3.07 (s, 1H), 3.55, 3.74 (dd, 2H), 3.90–4.00 (m, 2H), 4.02 (s, 1H), 4.11–4.13 (m, 1H), 4.48–4.52 (m, 1H), 4.65–4.75 (s, 2H), 5.65 (d, 1H), 6.75–6.82 (m, 3H), 7.08–7.12 (m, 2H), 7.94 (s, 1H).

EXAMPLE 9

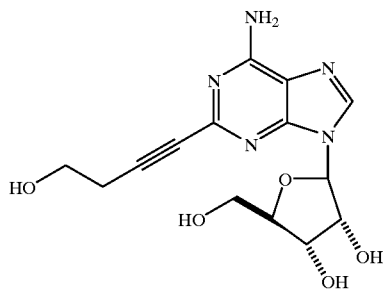

(4S,2R,3R,5R)-2-[6-amino-2-(4-hydroxybut-1-ynyl)purin-9-yl]-5-(hydroxymethyl)oxolane-3,4-diol (18)

Compound 18 was prepared in the manner of compound 10. $^1$H NMR(CDCl$_3$:CD$_3$OD 9:1) δ2.45–2.55 (m, 2H), 3.02–3.04 (m, 1H), 3.07 (s, 1H), 3.55, 3.74 (dd, 2H), 4.02 (s, 1H), 4.11–4.13 (m, 1H), 4.48–4.52 (m, 1H), 4.65–4.73 (m, 2H), 5.65 (d, 1H), 7.94 (s, 1H).

EXAMPLE 10

Compositions of this invention were assayed to determine their affinity for the A$_{2A}$ receptor in a pig striatum membrane prep. 0.2 mg of pig striatal membranes were treated with adenosine deaminase and 50 mM Tris buffer (pH=7.4) followed by mixing. To the pig membranes was added 2 μL of serially diluted DMSO stock solution of the compounds of this invention at concentrations ranging from 100 μM to 10 nM or the control received 2 μL of DMSO alone, then the tritiated antagonist ZM 241385 in Tris buffer (50 mM, pH of 7.4) was added to achieve a final concentration of 2 nM . After incubation at 23° C. for 2 h, the solutions were filtered using a membrane harvester using multiple washing of the membranes (3x). The filter disks where counted in scintillation cocktail affording the amount of displacement of tritiated ZM by the competitive binding compositions of this invention. Greater than a 5 point curve was used to generate IC50's and the number of experiments (n) is indicated in the column marked in Table 1 below.

TABLE 1

| Compound Number | Ki (nM) | n |
|---|---|---|
| 10 | + + | 2 |
| 11 | + + + | 4 |
| 12 | + + | 3 |
| 13 | + | 3 |
| 14 | + + | 3 |
| 15 | + + + | 1 |
| 16 | + | 2 |

+ + + = 10–100 nM
+ + = 100–1,000 nM
+ = 1,000–10,000 nM

These results indicate that the compositions of this invention are potent enough to be useful as vasodilators.

EXAMPLE 11

The compounds of Tables 2–5 my be prepared using the synthesis schemes described above:

TABLE 2

| | $R_2$, $R_3$, and $R_4$ = H; | |
|---|---|---|
| $R_1$ | $R_5$ | $R_6$ |
| CH$_2$OH | 3-methoxy | 5-methoxy |
| CH$_2$OH | 3-ethoxy | 5-ethoxy |
| CH$_2$OH | 3-propoxy | 5-propoxy |
| CH$_2$OH | 3-iso-propoxy | 5-iso-propoxy |
| CH$_2$OH | 3-methyl | 5-methyl |
| CH$_2$OH | 3-ethyl | 5-ethyl |
| CH$_2$OH | 3-propyl | 5-propyl |
| CH$_2$OH | 3-iso propyl | 5-iso propyl |
| CH$_2$OH | 3-methyl | 5-isopropyl |
| CH$_2$OH | 3-trifluoromethyl | 5-trifluoromethyl |
| CH$_2$OH | 3-chloro | 5-chloro |
| CH$_2$OH | 3-fluoro | 5-fluoro |
| CH$_2$OH | 2-methoxy | 3-methoxy |
| CH$_2$OH | 2-methyl | 3-methyl |
| CH$_2$OH | 3-methoxy | 4-methoxy |

TABLE 3

| $R_2$, $R_3$, $R_4$, and $R_5$ = H; | |
|---|---|
| $R_1$ | $R_6$ |
| CH$_2$OH | 3-methyl |
| CH$_2$OH | 3-ethyl |
| CH$_2$OH | 3-propyl |
| CH$_2$OH | 3-iso-propyl |
| CH$_2$OH | 3-sec-butyl |
| CH$_2$OH | 3-tert-butyl |
| CH$_2$OH | 3-trifluoromethyl |
| CH$_2$OH | 4-tert--butyl |
| CH$_2$OH | 4-chloro |
| CH$_2$OH | 4-fluoro |

TABLE 4

| | $R_2$, $R_3$, and $R_4$ = H; | |
|---|---|---|
| $R_1$ | $R_5$ | $R_6$ |
| C(O)NHEt | 3-methoxy | 5-methoxy |
| C(O)NHEt | 3-ethoxy | 5-ethoxy |
| C(O)NHEt | 3-propoxy | 5-propoxy |
| C(O)NHEt | 3-iso-propoxy | 5-iso-propoxy |
| C(O)NHEt | 3-methyl | 5-methyl |

TABLE 4-continued

| | $R_2$, $R_3$, and $R_4$ = H; | |
|---|---|---|
| $R_1$ | $R_5$ | $R_6$ |
| C(O)NHEt | 3-ethyl | 5-ethyl |
| C(O)NHEt | 3-propyl | 5-propyl |
| C(O)NHEt | 3-iso propyl | 5-iso propyl |
| C(O)NHEt | 3-methyl | 5-isopropyl |
| C(O)NHEt | 3-trifluoromethyl | 5-trifluoromethyl |
| C(O)NHEt | 3-chloro | 5-chloro |
| C(O)NHEt | 3-fluoro | 5-fluoro |
| C(O)NHEt | 2-methoxy | 3-methoxy |
| C(O)NHEt | 2-methyl | 3-methyl |
| C(O)NHEt | 3-methoxy | 4-methoxy |

TABLE 5

| $R_2$, $R_3$, $R_4$, and $R_5$ = H; | |
|---|---|
| $R_1$ | $R_6$ |
| C(O)NHEt | 3-methyl |
| C(O)NHEt | 3-ethyl |
| C(O)NHEt | 3-propyl |
| C(O)NHEt | 3-iso-propyl |
| C(O)NHEt | 3-sec-butyl |
| C(O)NHEt | 3-tert-butyl |
| C(O)NHEt | 3-trifluoromethyl |
| C(O)NHEt | 4-tert--butyl |
| C(O)NHEt | 4-chloro |
| C(O)NHEt | 4-fluoro |

What we claim is:

1. A compound having the formula:

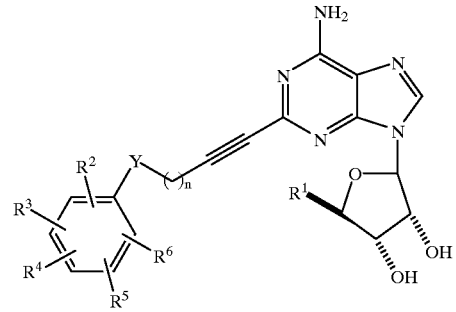

wherein
   n=1;
   Y=O;
   $R^1$ is —CH$_2$OH, or C(=O)NHEt;
   $R^2$, $R^3$, $R^4$, $R^5$, and $R^6$ are each individually selected from the group consisting of hydrogen, halo, CF$_3$, CN, OR$^{20}$, C$_{1-4}$ alkyl, heterocyclyl, and aryl, wherein the alkyl and aryl substituents are optionally substituted with aryl; wherein at least three substituents selected from the group consisting of $R^2$, $R^3$, $R^4$, $R^5$, and $R^6$ are hydrogen; and
   $R^{20}$ is selected from the group consisting of H and C$_{1-3}$ alkyl.

2. The compound of claim 1 wherein
   $R^1$=CH$_2$OH;
   $R^2$, $R^3$, $R^4$, $R^5$, and $R^6$ are each individually selected from the group consisting of hydrogen, halo, CF$_3$, CN, OR$^{20}$, C$_{1-4}$ alkyl optionally substituted with aryl and a five to seven membered ring formed by the combination of one pair of adjacent substituents selected from the group consisting of $R^2$ and $R^3$, $R^3$ and $R^4$, $R^4$ and $R^5$, $R^5$ and $R^6$, and $R^6$ and $R^2$ wherein the five to seven membered ring my contain from 1 to 3 heteroatoms selected from the group consisting of O, N, S, and combinations thereof; and $R^{20}$ is selected from the group consisting of H, and $C_{1-3}$ alkyl.

3. The compound of claim 1 wherein $R^1$=$CH_2OH$;

$R^2$, $R^3$, $R^4$, $R^5$, and $R^6$ are each individually selected from the group consisting of hydrogen, halo, $CF_3$, CN, $OR^{20}$, $C_{1-4}$ alkyl and aryl optionally substituted with a substituent selected from the group consisting of aryl and a five to seven membered ring formed by the combination of one pair of adjacent substituents selected from the group consisting of $R^2$ and $R^3$, $R^3$ and $R^4$, $R^4$ and $R^5$, $R^5$ and $R^6$, and $R^6$ and $R^2$ wherein the fused five membered rings contain two non-adjacent oxygen atoms; and $R^{20}$ is selected from the group consisting of H, and $C_{1-3}$ alkyl.

4. The compound of claim 1 wherein $R^1$=$CH_2OH$, and $R^2$, $R^3$, $R^4$, $R^5$, and $R^6$ are each individually selected from the group consisting of hydrogen, CN, and $C_{1-4}$ alkyl optionally substituted with aryl and a five membered ring formed by the combination of one pair of adjacent substituents selected from the group consisting of $R^2$ and $R^3$, $R^3$ and $R^4$, $R^4$ and $R^5$, $R^5$ and $R^6$, or $R^6$ and $R^2$ wherein the fused five membered rings contain two non-adjacent oxygen atoms.

5. The compound of claim 1 wherein $R^1$=C(O)NHEt;

$R^2$, $R^3$, $R^4$, $R^5$, and $R^6$ are each individually selected from the group consisting of hydrogen, halo, $CF_3$, CN, $OR^{20}$, aryl, and $C_{1-4}$ alkyl that is optionally substituted with one substituent selected from the group consisting of aryl and a five membered ring formed by the combination of one pair of adjacent substituents selected from the group consisting of $R^2$ and $R^3$, $R^3$ and $R^4$, $R^4$ and $R^5$, $R^5$ and $R^6$, or $R^6$ and $R^2$ wherein the fused five membered rings contain two non-adjacent oxygen atoms; and $R^{20}$ is a selected from the group consisting of H, and $C_{1-3}$ alkyl.

6. The compound of claim 1 wherein $R^1$=C(O)NHEt;

$R^2$, $R^3$, $R^4$, $R^5$, and $R^6$ are each individually selected from the group consisting of hydrogen, CN, aryl, and $C_{1-4}$ alkyl that is optionally substituted with one substituent selected from the group consisting of aryl, and a five membered ring formed by the combination of one pair of adjacent substituents selected from the group consisting of $R^2$ and $R^3$, $R^3$ and $R^4$, $R^4$ and $R^5$, $R^5$ and $R^6$, and $R^6$ and $R^2$ wherein the five membered rings contain two non-adjacent oxygen atoms.

7. The compound of claim 1 wherein $R^1$=C(O)NHEt;

$R^2$, $R^3$, $R^4$, $R^5$, and $R^6$ are each individually selected from the group consisting of hydrogen, CN, aryl, and $C_{1-4}$ alkyl that is optionally substituted with aryl, wherein $R^2$ and $R^3$ may together form a fused five membered ring containing two non-adjacent oxygen atoms.

8. The compound of claim 7 wherein four substitutents selected from the group consisting of $R^2$, $R^3$, $R^4$, $R^5$, and $R^6$ are hydrogen.

9. The compound of claim 1 wherein $R^1$=$CH_2OH$;

$R^2$, $R^3$, $R^4$, $R^5$, and $R^6$ are each individually selected from the group consisting of hydrogen, halo, $CF_3$, CN, $OR^{20}$, $C_{1-8}$ alkyl, heterocyclyl, and aryl, wherein the alkyl, aryl, and heterocyclyl substituents are optionally substituted with one substituent selected from the group consisting of halo, aryl, $CF_3$, CN, and $OR^{20}$, and wherein each optional substituted aryl substituent is further optionally substituted with a moiety selected from the group consisting of halo, alkyl, CN, and $CF_3$; and $R^{20}$ is selected from the group consisting of H, and $C_{1-3}$ alkyl.

10. The compound of claim 1 wherein $R^1$=$CH_2OH$;

$R^2$, $R^3$, $R^4$, $R^5$, and $R^6$ are each individually selected from the group consisting of hydrogen, halo, $CF_3$, CN, $OR^{20}$, $C_{1-6}$ alkyl, heterocyclyl, and aryl, wherein the optional alkyl, and aryl substituents are optionally substituted with one substituent selected from the group consisting of halo, aryl, $CF_3$, CN, and $OR^{20}$; and $R^{20}$ is selected from the group consisting of H, and $C_{1-3}$alkyl.

11. The composition of claim 1 wherein $R^1$=$CH_2OH$;

$R^2$, $R^3$, $R^4$, $R^5$, and $R^6$ are each individually selected from the group consisting of hydrogen, halo, $CF_3$, CN, $OR^{20}$, $C_{1-4}$ alkyl, heterocyclyl, and aryl, wherein the alkyl and aryl substituents are optionally substituted with aryl; and $R^{20}$ is selected from the group consisting of H and $C_{1-3}$ alkyl.

12. The compound of claim 1 wherein $R^1$=C(O)NHEt;

$R^2$, $R^3$, $R^4$, $R^5$, and $R^6$ are each individually selected from the group consisting of hydrogen, halo, $CF_3$, CN, $OR^{20}$, $C_{1-8}$ alkyl, heterocyclyl, and aryl wherein the alkyl, aryl, and heterocyclyl substituents are optionally substituted with a substituent selected from the group consisting of halo, aryl, $CF_3$, CN, and $OR^{20}$, wherein each optional substituted aryl substituent is further optionally substituted with a substituent selected from the group consisting of halo, alkyl, CN, and $CF_3$; and $R^{20}$ is selected from the group consisting of H, and $C_{1-3}$ alkyl.

13. The composition of claim 1 wherein $R^1$=C(O)NHEt;

$R^2$, $R^3$, $R^4$, $R^5$, and $R^6$ are each individually selected from the group consisting of hydrogen, halo, $CF_3$, CN, $OR^{20}$, $C_{1-6}$ alkyl, heterocyclyl, and aryl, wherein the alkyl and aryl substituents are optionally substituted with one substituent selected from the group consisting of halo, aryl, $CF_3$, CN, and $OR^{20}$; and $R^{20}$ is selected from the group consisting of H, and $C_{1-3}$ alkyl.

14. The compound of claim 1 wherein $R^1$=C(O)NHEt;

$R^2$, $R^3$, $R^4$, $R^5$, and $R^6$ are each individually selected from the group consisting of hydrogen, halo, $CF_3$, CN, $OR^{20}$, $C_{1-4}$ alkyl, heterocyclyl, and aryl, wherein the alkyl and aryl substituents are optionally substituted with one aryl substituent; and $R^{20}$ is selected from the group consisting of H, and $C_{1-3}$ alkyl.

15. The compound of claim 4 wherein four substituents selected from the group consisting of $R^2$, $R^3$, $R^4$, $R^5$, and $R^6$ are hydrogen.

16. A compound having the formula:

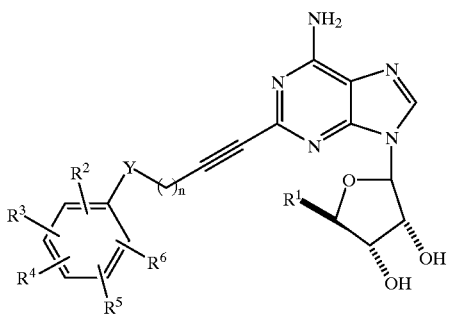

wherein
n=1 to 2;
Y=O, NH, or S;
$R^1$ is —$CH_2OH$, or —C(=O)$NR^7R^8$;
$R^2$, $R^3$, $R^4$, $R^5$, and $R^6$ are each individually selected from the group consisting of hydrogen, halo, $CF_3$, CN, $OR^{20}$, $SR^{20}$, $N(R^{20})_2$, $C_{1-15}$ alkyl, heterocyclyl, and aryl, wherein the alkyl, aryl, and heterocyclyl substituents are further optionally substituted with from 1 to 2 substituents independently selected from the group consisting of halo, aryl, $CF_3$, CN, $OR^{20}$, $SR^{20}$, and $N(R^{20})_2$, and wherein each optional substituted aryl substituent is further optionally substituted with a moiety selected from the group consisting of halo, alkyl, CN, and $CF_3$;
$R^7$ and $R^8$ are each individually selected from the group consisting of H, and $C_{1-8}$ alkyl; and
$R^{20}$ is selected from the group consisting of H, and $C_{1-3}$ alkyl.

17. The compound of claim 16 wherein at least one substituent selected from the group consisting of $R^2$, $R^3$, $R^4$, $R^5$, and $R^6$ is hydrogen.

18. The compound of claim 16 wherein at least two substituents selected from the group consisting of $R^2$, $R^3$, $R^4$, $R^5$, and $R^6$ are hydrogen.

19. A method for stimulating coronary vasodilatation in a mammal by administering to the mammal a therapeutically effective amount of a compound of claim 15 that is sufficient to stress the heart and induce a coronary steal situation for the purposes of imaging the heart.

20. The method of claim 19 wherein the therapeutically effective amount ranges from about 0.01 to about 100 mg/kg weight of the mammal.

21. The method of claim 19 wherein the mammal is a human.

22. A pharmaceutical composition comprising a compound of claim 16 in combination with a pharmaceutically acceptable carrier.

23. The pharmaceutical composition of claim 22 wherein the pharmaceutical composition is in the form of a solution.

24. A method for treating a human host in need thereof comprising administering a therapeutic amount of a pharmaceutical composition of claim 22 to a human in order to treat a condition selected from the group consisting of providing adjunctive therapy with angioplasty, inducing arterial dilation, inhibiting platelet aggregation, treating inflammation and reversing a blood clotting condition also known as no reflow.

25. The compound of claim 15 wherein the compound is selected from the group consisting of (4S,2R,3R,5R)-2-{6-amino-2-[3-(2-phenylphenoxy)prop-1-ynyl]purin-9-yl}-5-(hydroxymethyl)oxolane-3,4-diol; (4S,2R,3R,5R)-2-[6-amino-2-(3-phenoxyprop-1-ynyl)purin-9-yl]-5-(hydroxymethyl)oxolane-3,4-diol; 4-(3-{9-[(4S,2R,3R,5R)-3,4-dihydroxy-5-(hydroxymethyl)oxolan-2-yl]-6-aminopurin-2-yl}prop-2-ynyloxy)benzenecarbonitrile; (4S,2R,3R,5R)-2-{6-amino-2-[3-(4-phenylphenoxy)prop-1-ynyl]purin-9-yl}-5-(hydroxymethyl)oxolane-3,4-diol; (4S,2R,3R,5R)-2-(6-amino-2-{3-[2-benzylphenoxy]prop-1-ynyl}purin-9-yl)-5-(hydroxymethyl)oxolane-3,4-diol; 2-[2-(3-(2H-benzo[2,3-d]1,3-dioxolen-4-yloxy)prop-1-ynyl)-6-aminopurin-9-yl](4S,2R,3R,5R)-5-(hydroxymethyl)oxolane-3,4-diol; and (4S,2R,3R,5R)-2-(6-amino-2-{3-[3,5-bis(tert-butyl)phenoxy]prop-1-ynyl}purin-9-yl)-5-(hydroxymethyl)oxolane-3,4-diol.

* * * * *